(12) United States Patent
Arunachalam (10) Patent No.: US 10,557,839 B2
(45) Date of Patent: Feb. 11, 2020

(54) MULTI-SENSE ENVIRONMENTAL MONITORING DEVICE AND METHOD

(71) Applicant: Industrial Scientific Corporation, Pittsburgh, PA (US)

(72) Inventor: Raghu Arunachalam, Pittsburgh, PA (US)

(73) Assignee: Industrial Scientific Corporation, Pittsburgh, PA (US)

( * ) Notice: Subject to any disclaimer, the term of this patent is extended or adjusted under 35 U.S.C. 154(b) by 0 days.

(21) Appl. No.: 15/376,823

(22) Filed: Dec. 13, 2016

(65) Prior Publication Data

US 2017/0102369 A1 Apr. 13, 2017

Related U.S. Application Data

(63) Continuation of application No. 14/676,443, filed on Apr. 1, 2015, now Pat. No. 9,575,043, which is a
(Continued)

(51) Int. Cl.
*G01N 33/00* (2006.01)
*G08B 21/16* (2006.01)
(Continued)

(52) U.S. Cl.
CPC ..... *G01N 33/0063* (2013.01); *G01N 33/0006* (2013.01); *G08B 5/22* (2013.01);
(Continued)

(58) Field of Classification Search
CPC .......... G01N 33/0063; G01N 33/0006; G01N 33/0009; G08B 21/14; G08B 21/182
See application file for complete search history.

(56) References Cited

U.S. PATENT DOCUMENTS

| 1,797,891 A | 3/1931 | Young et al. |
| 4,416,911 A | 11/1983 | Wilkinson-Tough |

(Continued)

FOREIGN PATENT DOCUMENTS

| AU | 2017219135 B2 | 11/2018 |
| CA | 2803246 A1 | 12/2011 |

(Continued)

OTHER PUBLICATIONS

"RECON/4 Manual", ENMET Corporation, Jun. 22, 2009, p. 1-10.
(Continued)

*Primary Examiner* — Hongmin Fan
(74) *Attorney, Agent, or Firm* — GTC Law Group PC & Affiliates (57) ABSTRACT

Environmental monitoring devices for detecting and warning users of unhealthy levels of a given substance are disclosed having more than one sensor for each substance to be detected. A processing unit, wirelessly coupled to the sensors in the devices can be configured to receive each of the output signals from the sensors, determine a detection signal for the substance based on the output signals, determine a gain of a majority of the sensors, and generate a calibration action responsive to the output signals deviating by a threshold amount, wherein the calibration action comprises adjusting a gain of a deviating sensor to correspond with the gain of the majority of sensors.

6 Claims, 7 Drawing Sheets

Related U.S. Application Data continuation of application No. 13/168,577, filed on Jun. 24, 2011, now Pat. No. 9,000,910.

(60) Provisional application No. 61/358,729, filed on Jun. 25, 2010.

(51) Int. Cl.

| | | |
|---|---|---|
| *G08B 29/16* | (2006.01) | |
| *G08B 29/24* | (2006.01) | |
| *G08B 21/14* | (2006.01) | |
| *G08B 5/22* | (2006.01) | |
| *G08B 21/18* | (2006.01) | |
| *G08B 29/26* | (2006.01) | |

(52) U.S. Cl.
CPC ............ *G08B 21/14* (2013.01); *G08B 21/16* (2013.01); *G08B 21/182* (2013.01); *G08B 29/16* (2013.01); *G08B 29/24* (2013.01); *G08B 29/26* (2013.01)

(56) References Cited

U.S. PATENT DOCUMENTS

| | | | |
|---|---|---|---|
| 4,457,954 A | | 7/1984 | Dabill et al. |
| 4,473,797 A | * | 9/1984 | Shiota ............... G01J 1/44 324/115 |
| 4,525,872 A | | 6/1985 | Zochowski et al. |
| 4,775,083 A | | 10/1988 | Burger et al. |
| 4,931,780 A | | 5/1990 | Lamont et al. |
| 4,963,855 A | | 10/1990 | Kojima et al. |
| 5,005,419 A | | 4/1991 | O'Donnell et al. |
| 5,101,271 A | * | 3/1992 | Andrews ............ H04N 5/367 250/252.1 |
| 5,138,559 A | | 8/1992 | Kuehl et al. |
| 5,243,152 A | | 9/1993 | Magid et al. |
| 5,493,273 A | * | 2/1996 | Smurlo ............... G08B 29/16 340/309.16 |
| 5,568,121 A | | 10/1996 | Lamensdorf |
| 5,778,062 A | | 7/1998 | Vanmoor et al. |
| 5,916,180 A | * | 6/1999 | Cundari ............... A61B 5/0053 600/587 |
| 5,932,176 A | | 8/1999 | Yannopoulos et al. |
| 6,182,497 B1 | | 2/2001 | Krajci |
| 6,466,608 B1 | | 10/2002 | Hong et al. |
| 6,629,152 B2 | | 9/2003 | Kingsbury et al. |
| 6,644,098 B2 | | 11/2003 | Cardinale et al. |
| 6,649,876 B2 | | 11/2003 | Cardinale |
| 6,703,840 B2 | | 3/2004 | Cardinale |
| 6,822,573 B2 | | 11/2004 | Basir et al. |
| 7,020,508 B2 | | 3/2006 | Stivoric et al. |
| 7,463,142 B2 | | 12/2008 | Lindsay et al. |
| 7,471,200 B2 | | 12/2008 | Otranen |
| 7,587,619 B2 | | 9/2009 | Ryan |
| 7,613,156 B2 | | 11/2009 | Rittle et al. |
| 7,649,872 B2 | | 1/2010 | Naghian et al. |
| 7,688,802 B2 | | 3/2010 | Gonia et al. |
| 7,697,893 B2 | | 4/2010 | Kossi et al. |
| 7,778,431 B2 | | 8/2010 | Feng et al. |
| 7,880,607 B2 | | 2/2011 | Olson et al. |
| 7,885,291 B2 | | 2/2011 | Delaney |
| 7,888,825 B2 | | 2/2011 | Koshi et al. |
| 7,895,309 B2 | | 2/2011 | Belali et al. |
| 7,917,673 B2 | | 3/2011 | Suh |
| 7,970,871 B2 | | 6/2011 | Ewing et al. |
| 7,978,717 B2 | | 7/2011 | Banks et al. |
| 8,009,437 B2 | | 8/2011 | Shelton et al. |
| 8,035,491 B2 | | 10/2011 | Banks |
| 8,081,590 B2 | | 12/2011 | Patterson et al. |
| 8,085,144 B2 | | 12/2011 | Appelt et al. |
| 8,086,285 B2 | | 12/2011 | McNamara et al. |
| 8,180,075 B2 | | 5/2012 | Nelson et al. |
| 8,204,971 B2 | | 6/2012 | Ewing et al. |
| 8,224,246 B2 | | 7/2012 | Suumaki et al. |
| 8,294,568 B2 | | 10/2012 | Barrett et al. |
| 8,358,214 B2 | | 1/2013 | Gingrave et al. |
| 8,385,322 B2 | | 2/2013 | Colling et al. |
| 8,400,317 B2 | | 3/2013 | Johnson et al. |
| 8,416,120 B2 | * | 4/2013 | Kim ..................... G01S 5/0289 342/118 |
| 8,418,064 B2 | | 4/2013 | Guagenti et al. |
| 8,438,250 B2 | | 5/2013 | Ewing et al. |
| 8,442,801 B2 | | 5/2013 | Gonla et al. |
| 8,462,707 B2 | | 6/2013 | Husney |
| 8,494,502 B2 | | 7/2013 | Abel et al. |
| 8,514,087 B2 | | 8/2013 | Little et al. |
| 8,547,888 B2 | | 10/2013 | Filoso et al. |
| 8,585,606 B2 | | 11/2013 | McDonald et al. |
| 8,587,414 B2 | | 11/2013 | Bandyopadhyay et al. |
| 8,638,228 B2 | | 1/2014 | Amigo et al. |
| 8,665,097 B2 | | 3/2014 | Stinson et al. |
| 8,792,401 B2 | | 7/2014 | Banks et al. |
| 8,805,430 B2 | | 8/2014 | Olsen et al. |
| 8,818,397 B2 | | 8/2014 | Shikowitz et al. |
| 8,868,703 B2 | | 10/2014 | Ewing et al. |
| 8,885,513 B2 | | 11/2014 | Ewing |
| 9,000,910 B2 | | 4/2015 | Arunachalam |
| 9,195,866 B1 | | 11/2015 | Mehranfar et al. |
| 9,536,418 B2 | | 1/2017 | Mao et al. |
| 9,575,043 B2 | | 2/2017 | Arunachalam |
| 9,743,221 B2 | | 2/2017 | Javer et al. |
| 9,619,986 B2 | | 4/2017 | Seol |
| 9,721,456 B2 | | 8/2017 | Thurlow et al. |
| 9,792,808 B2 | | 10/2017 | Gnanasekaran et al. |
| 9,847,008 B2 | | 12/2017 | Hunter et al. |
| 10,055,971 B2 | | 8/2018 | M R et al. |
| 10,062,260 B2 | | 8/2018 | Hunter et al. |
| 2001/0050612 A1 | | 12/2001 | Shaffer |
| 2002/0009195 A1 | | 1/2002 | Schon et al. |
| 2002/0126002 A1 | | 9/2002 | Patchell et al. |
| 2002/0146352 A1 | | 10/2002 | Wang et al. |
| 2002/0155622 A1 | | 10/2002 | Slater et al. |
| 2003/0150252 A1 | | 8/2003 | Wang et al. |
| 2003/0159497 A1 | | 8/2003 | Warburton et al. |
| 2003/0180445 A1 | | 9/2003 | Wang et al. |
| 2005/0083194 A1 | | 4/2005 | Shen et al. |
| 2005/0202582 A1 | * | 9/2005 | Eversmann ....... G01N 33/48728 438/48 |
| 2005/0243794 A1 | | 11/2005 | Yoon et al. |
| 2006/0019402 A1 | | 1/2006 | Wang et al. |
| 2006/0224357 A1 | | 10/2006 | Taware et al. |
| 2006/0257289 A1 | | 11/2006 | Martens et al. |
| 2007/0000310 A1 | | 1/2007 | Yamartino et al. |
| 2007/0078608 A1 | | 4/2007 | Broy et al. |
| 2007/0171042 A1 | | 7/2007 | Metes et al. |
| 2007/0241261 A1 | * | 10/2007 | Wendt ................. G01D 9/005 250/221 |
| 2007/0257806 A1 | * | 11/2007 | Madden ............... G01N 33/18 340/603 |
| 2008/0015794 A1 | * | 1/2008 | Eiler ..................... F24F 3/16 702/33 |
| 2008/0038590 A1 | | 2/2008 | Nakakubo et al. |
| 2008/0058614 A1 | | 3/2008 | Banet et al. |
| 2008/0122641 A1 | | 5/2008 | Amidi et al. |
| 2008/0146895 A1 | | 6/2008 | Olson et al. |
| 2008/0240463 A1 | | 10/2008 | Florencio et al. |
| 2009/0089108 A1 | | 4/2009 | Angell et al. |
| 2009/0115654 A1 | | 5/2009 | Lo et al. |
| 2009/0210257 A1 | | 8/2009 | Chalfant et al. |
| 2009/0312976 A1 | | 12/2009 | Bingham et al. |
| 2010/0072334 A1 | | 3/2010 | Le Gette et al. |
| 2010/0267407 A1 | | 10/2010 | Liao et al. |
| 2011/0022421 A1 | | 1/2011 | Brown et al. |
| 2011/0115623 A1 | | 5/2011 | Gnanasekaran et al. |
| 2011/0161885 A1 | | 6/2011 | Gonia et al. |
| 2012/0150755 A1 | | 6/2012 | Kumar et al. |
| 2012/0176237 A1 | | 7/2012 | Tabe et al. |
| 2013/0006064 A1 | | 1/2013 | Reiner et al. |
| 2013/0057391 A1 | | 3/2013 | Salvador et al. |
| 2013/0253809 A1 | | 9/2013 | Jones et al. |
| 2013/0278412 A1 | | 10/2013 | Kelly et al. |
| 2014/0122537 A1 | | 5/2014 | Stivoric et al. |
| 2014/0233458 A1 | | 8/2014 | Georgescu et al. |

(56) References Cited

U.S. PATENT DOCUMENTS

| | | |
|---|---|---|
| 2014/0274155 A1 | 9/2014 | Langberg |
| 2014/0310349 A1 | 10/2014 | Rainisto |
| 2014/0368354 A1 | 12/2014 | Skourlis |
| 2015/0025917 A1 | 1/2015 | Stempora |
| 2015/0145649 A1 | 5/2015 | Michaud et al. |
| 2015/0145685 A1 | 5/2015 | Albinger et al. |
| 2015/0161876 A1 | 6/2015 | Castillo |
| 2015/0163652 A1 | 6/2015 | Michaud et al. |
| 2016/0209386 A1 | 7/2016 | Belski et al. |
| 2016/0334378 A1 | 11/2016 | Maddila et al. |
| 2017/0132884 A1 | 5/2017 | Kumar et al. |
| 2017/0303187 A1 | 10/2017 | Crouthamel et al. |
| 2018/0024091 A1 | 1/2018 | Wang et al. |
| 2018/0082565 A1 | 3/2018 | Braiman |

FOREIGN PATENT DOCUMENTS

| | | |
|---|---|---|
| CN | 2135808 Y | 6/1993 |
| CN | 104903953 A | 9/2015 |
| CN | 105092796 B | 12/2018 |
| EP | 2586018 A1 | 5/2013 |
| EP | 3227808 A1 | 10/2017 |
| EP | 3228068 A1 | 10/2017 |
| EP | 2287789 B1 | 11/2017 |
| EP | 3510386 A1 | 7/2019 |
| GB | 2423400 A | 8/2006 |
| JP | 2002344602 A | 11/2002 |
| JP | 2007193773 A | 8/2007 |
| WO | 1995026492 A1 | 10/1995 |
| WO | 2008111755 A1 | 9/2008 |
| WO | 2011163604 A1 | 12/2011 |
| WO | 2014184638 A1 | 11/2014 |
| WO | 2016005805 A1 | 1/2016 |
| WO | 2017142847 A1 | 8/2017 |
| WO | 2018048517 A1 | 3/2018 |
| WO | 2018165883 A1 | 9/2018 |

OTHER PUBLICATIONS

"Solaris Multigas Detector", "Solaris Multigas Detector", Solaris Mul tigas Manual, Jan. 1, 2005, p. 1-162.

"Wearable Sensors in Transportation—Exploratory Advanced Research Program Initial Stage Investigation", The Exploratory Advanced Research Program, Mar. 2016, 52 pages.

13741909.9, "European Application Serial No. 13741909.9, Communication pursuant to Article 94(3) EPC dated Jan. 4, 2017", Industrial Scientific Corporation, 7 Pages.

2013325257, "Australian Application Serial No. 2013325257, First Examination Report dated Jul. 24, 2017", Industrial Scientific Corporation, 3 Pages.

2015261602, "Australian Application Serial No. 2015261602, First Examiner Report dated Sep. 2, 2016", Industrial Scientific Corporation, 3 Pages.

2015261602, "Australian Application Serial No. 2015261602, Second Examiner Report dated Aug. 17, 2017", Industrial Scientific Corporation, 4 Pages.

Azhari, et al., "On the Performance of Off-Body Links for a Wireless Body Area Network in an Underground Mining Environment", International Journal of Computer Science and Innovation, vol. 2015, No. 2,, 2015, pp. 53-67.

Ding, et al., "Redundant Sensor Calibration Monitoring Using Independent Component Analysis and Pricipal Component Analysis", p. 27-47.

Dorsavi, "ViPerform—Provides Objective Data to Accurately Assess Risk of Injury, Guide Training Programs, and Help Determine When It's Safe to Return to Play", Available online at <http://us.dorsavi.com/viperform/>, retrieved on Jul. 10, 2016, 12 pages.

Giang, "Companies Are Putting Sensors on Employees to Track Their Every Move", http://www.businessinsider.com/tracking-employees-with-productivity-sensors-2013-3, Mar. 14, 2013, 1-4.

Giang, "Companies Are Putting Sensors on Employees to Track Their Every Move", Tracking Employees With Productivity Sensors—Business Insider, Available online at <http://www.businessinsider.com/tracking-employees-with-productivity-sensors-2013-3>, Mar. 14, 2013, pp. 1-4.

Mayton, et al., "TRUSS: Tracking Risk with Ubiquitous Smart Sensing", In 2012 IEEE Sensors, Institute of Electrical and Electronics Engineers (IEEE) 2012, pp. 1-4.

Peaksoft Technologies, "Big Idea Seeing Crime Before It Happens", Available online at <http://www.pstpl.com/news184.html>, Dec. 3, 2011, pp. 1-2.

2017219135, "Australian Application Serial No. 2017219135, First Examination Report dated Mar. 27, 2018", Industrial Scientific Corporation, 4 pages.

PCT/US2017/044735, "International Application Serial No. PCT/US2017/044735, International Search Report and Written Opinion dated Jan. 18, 2018", Industrial Scientific Corporation, 14 Pages.

PCT/US2017/044735, "International Application Serial No. PCT/US2017/044735, Invitation to Pay Additional Fees and, Where Applicable, Protest Fee dated Nov. 7, 2017", Industrial Scientific Corporation, 2 Pages.

PCT/US2017/044735, "International Application Serial No. PCT/US2017/044735, International Preliminary Report on Patentability and Written Opinion dated Mar. 21, 2019", Industrial Scientific Corporation, 6 pages.

* cited by examiner

MULTI-SENSE ENVIRONMENTAL MONITORING DEVICE AND METHOD

CROSS-REFERENCE TO RELATED APPLICATION

This application is a continuation of U.S. application Ser. No. 14/676,443, entitled "Multi-Sense Environmental Monitoring Device and Method", filed Apr. 1, 2015 which is a continuation of U.S. application Ser. No. 13/168,577 entitled "Multi-Sense Environmental Monitoring Device and Method," filed Jun. 24, 2011, which claims benefit of priority to U.S. Provisional Patent Application No. 61/358,729 filed on Jun. 25, 2010 entitled "Multi-Sense Environmental Monitoring Device and Method," the entire contents of which are hereby incorporated by reference in their entirety.

FIELD OF THE INVENTION

Embodiments of the present invention generally relate to environmental monitoring devices.

BACKGROUND OF THE INVENTION

In a number of industrial work environments workers are at risk of being exposed to a variety of hazardous environmental substances such as toxic or highly combustible gases, oxygen depleted environments, or radiation, etc. that pose a serious threat to worker safety. In order to keep workers safe, specialized environmental monitoring devices are used to alert workers of dangerous changes in their immediate environment.

Current practice involves using fixed point monitoring devices that monitor the environment around where they are deployed or portable monitoring devices that are carried by the workers to monitor their immediate vicinity. Fixed point monitoring devices are typically used around potential hazard locations such as confined spaces to warn workers of the environment before they enter. Portable monitoring devices are often used for personal protection. These monitoring devices may have a single sensor to monitor one specific substance or multiple sensors (typically two to six) each monitoring a distinct substance.

Given that these environmental monitoring devices are life critical, it is important the device functions properly and accurately. Current practice involves periodic bump testing and calibration of monitoring devices to guarantee proper functioning. Bump tests involve exposing the monitoring device to a measured quantity of gas and verifying that the device responds as designed, i.e., it senses the gas and goes into alarm. Calibration involves exposing the device to a measured quantity of gas and adjusting the gain of the sensors so it reads the quantity of gas accurately. The purpose of calibration is to maintain the accuracy of the monitoring device over time.

Current best practice followed by leading manufacturers of environmental monitors recommends bump testing the monitoring device before every days work and calibrating the device once at least every thirty days. While a number of manufacturers sell automated docking stations that automatically perform calibration and bump testing when a monitoring device is docked, there are still a number of disadvantages to the current practice.

A fixed bump and calibration policy, such as currently practiced, does not take into account the actual state of the sensors or the environmental monitoring device. Such a fixed policy (bump test every day and calibrate every thirty days) by its very nature is a compromise that is too stringent in many cases and too liberal in many others.

Given that the docking operation requires the user to bring the monitor to a central location, which typically is outside the work area, to perform the bump test and calibration, there is value in minimizing/optimizing this operation as much as possible without compromising safety.

Threshold limit values (TLV), namely the maximum exposure of a hazardous substance repeatedly over time which causes no adverse health effects in most people is constantly being reduced by regulatory authorities as scientific understanding and evidence grows and we accumulate more experience. Often these reductions are quite dramatic as in the case of the recent (February 2010) reduction recommended by the American Congress of Governmental Industrial Hygienists (ACGIH) for H2S exposure. The ACGIH reduced the TLV for H2S from a time weighted average (TWA) of 10 ppm to 1 ppm TWA averaged over eight hours. The effect of such reductions puts a premium on accuracy of measurements. Current practice of a fixed calibration policy, such as calibrate every thirty days, may not be enough to guarantee the level of accuracy to meet the more stringent emerging TLV's. While a blanket reduction in the frequency of the calibration interval, i.e., from thirty days, will help to improve accuracy, it would add significant cost to the use and maintenance of the environmental monitoring devices.

One solution to this problem, pursued by some, is to use newer and more advanced technology sensors with a higher degree of accuracy and tolerance to drift that minimize the need for calibration and bump testing. While there certainly is value in this approach, the cost of these emerging sensor often preclude its widespread use, particularly in personal monitoring applications where a large number of these monitors need to be deployed.

For all the aforementioned reasons there is value in developing monitors that use current low cost sensor technologies while still meeting emerging TLV regulations and allow for a more adaptive calibration/bump policy that takes into account the state of the sensors and monitoring devices.

SUMMARY OF THE INVENTION

In one general aspect, embodiments of the present invention generally pertain to a monitoring device having at least two sensors for each substance to be detected, a display, a processing unit, and an alarm. The sensors may be positioned on more than one plane or surface of the device. The processing unit may auto or self calibrate the sensors. Another embodiment relates to a network of monitoring devices. Other embodiments pertain to methods of monitoring a substance with a monitoring device having at least two sensors for that substance and auto or self calibrating the sensors.

Those and other details, objects, and advantages of the present invention will become better understood or apparent from the following description and drawings showing embodiments thereof.

BRIEF DESCRIPTION OF THE DRAWINGS

The accompanying drawings illustrate examples of embodiments of the invention. In such drawings.

DETAILED DESCRIPTION

Various embodiments of the present invention pertain to a monitoring device and methods used for environmental monitoring of substances, such as, for example and without limitation, gases, liquids, nuclear radiation, etc.

Figure 1A:
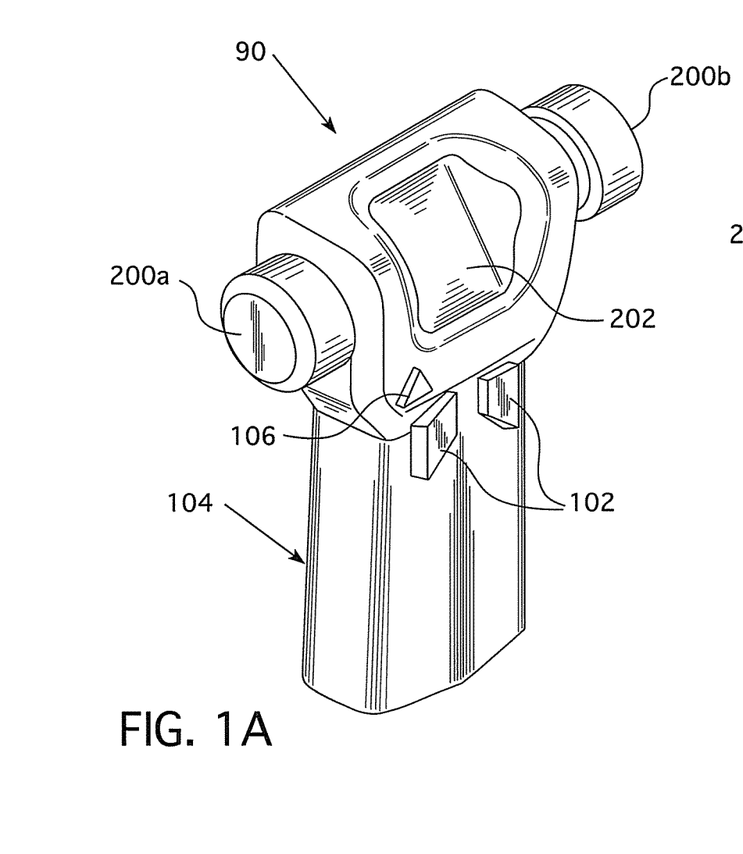
FIGS. 1A, 1B and 1C illustrate monitoring devices having two sensors that detect the same substance and positioned on different planes or surfaces of the device.
Figure 1B:
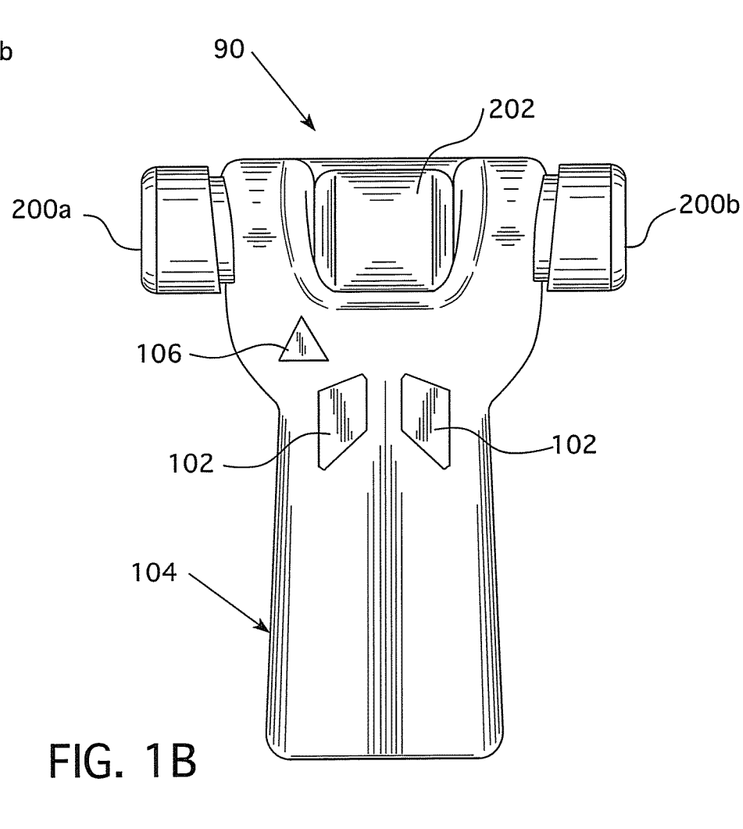
Figure 1C:
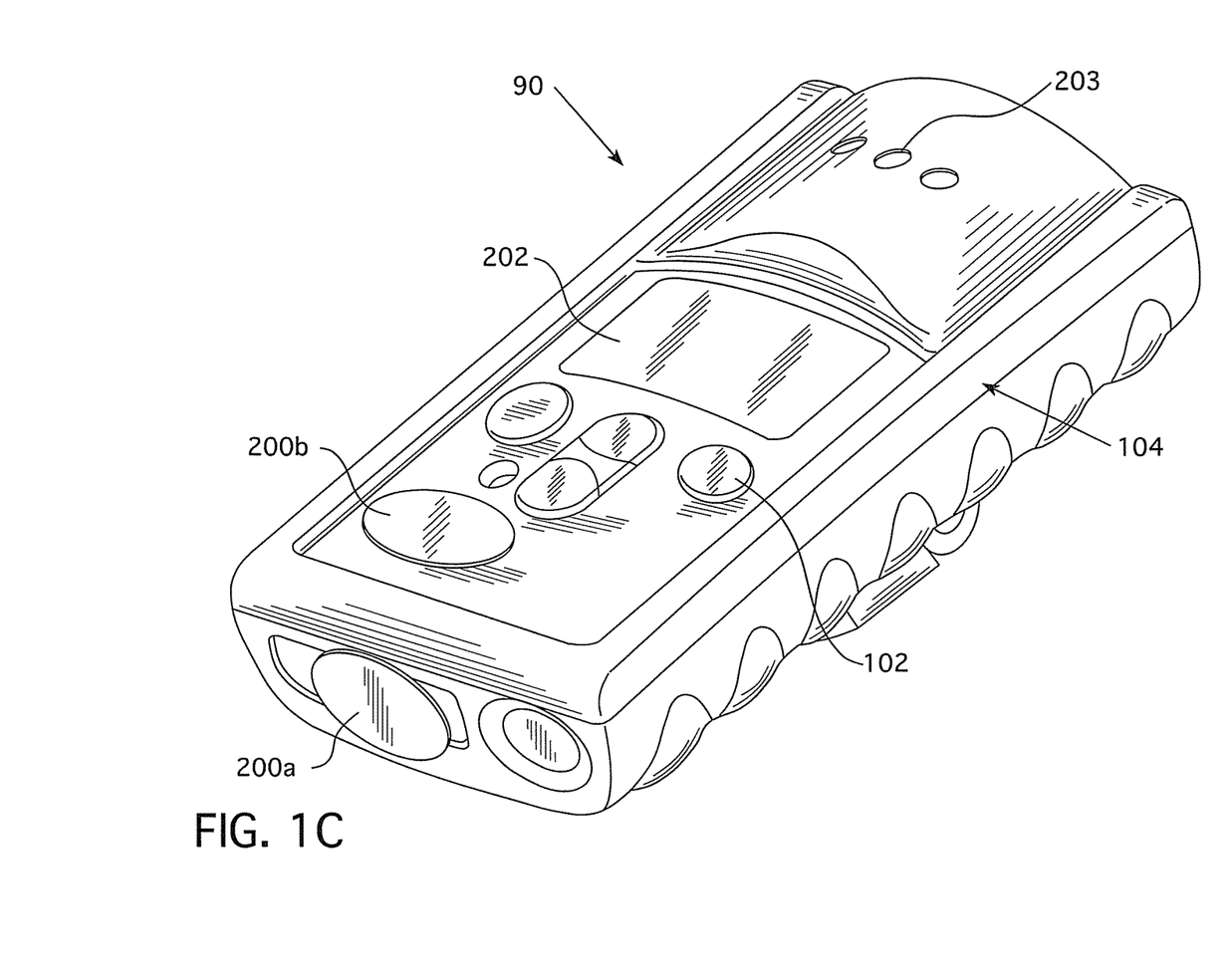
Figure 1D:
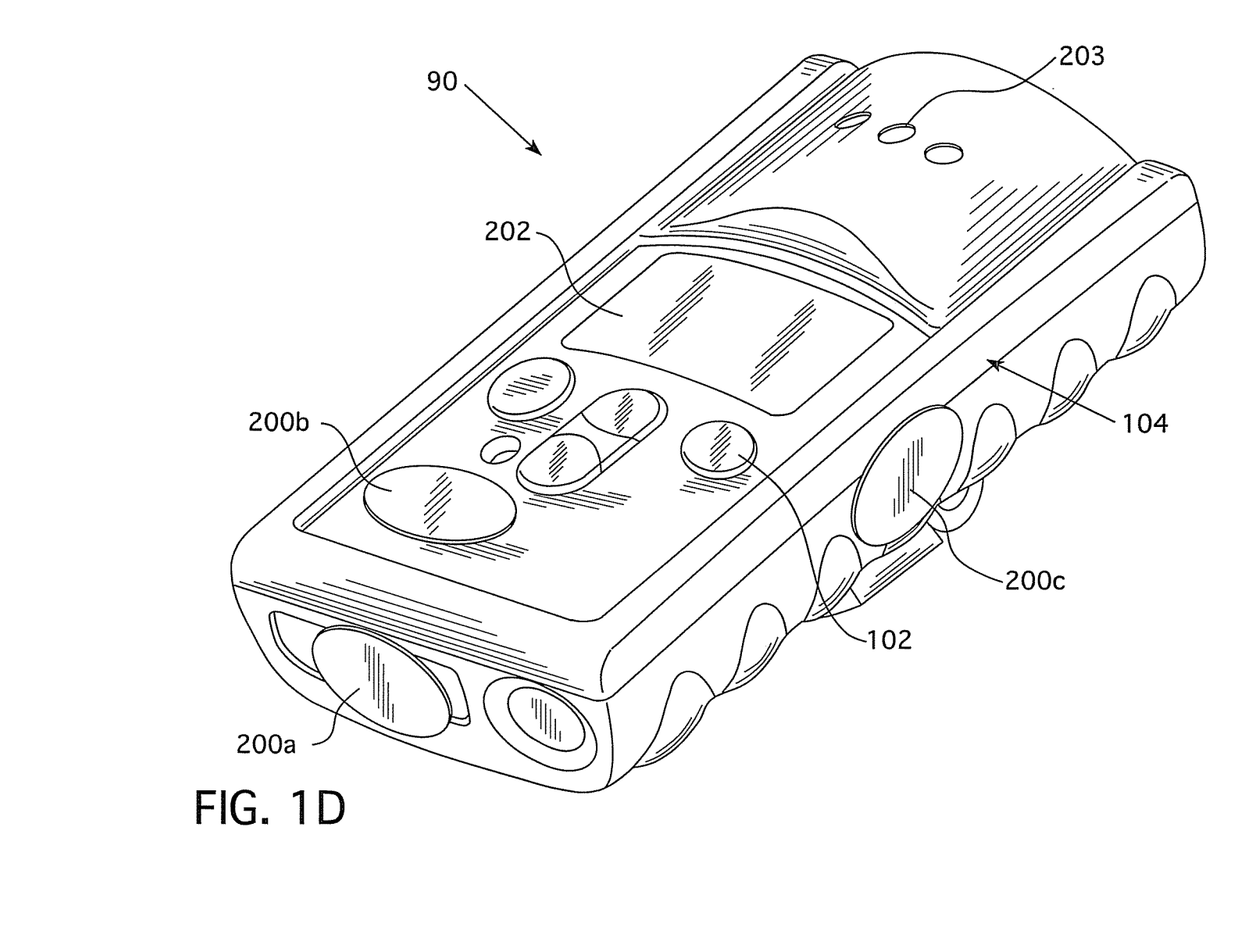
FIG. 1D shows a monitoring device having three sensors according to various embodiments of the present invention.

In an embodiment, as illustrated in FIGS. 1A-C, the monitoring device 90 has at least two sensors, 200a and 200b, which detect the same substance. The sensors may be positioned in more than one plane or surface of the device 90. The device 90 also has a display 202; a user interface 102, such as, for example and without limitation, at least one key or key pad, button, or touch screen, for control and data entry; an alarm 203, shown in FIGS. 1C and 1D, such as, for example and without limitation, audio, visual, or vibration; and a housing 104. The monitoring device 90 may have a user panic button 106, shown in FIGS. 1A and 1B, that allows the user to trigger an alarm mechanism. In an example, as shown in FIGS. 1A and 1B, sensor 200a and 200b are on opposite sides of the device 90. In another example, as shown in FIG. 1C, sensor 200a is on the front of the device 90 and sensor 200b on the top. In yet another example, as shown in FIG. 1D, the device 90 has three sensors, 200a-c, sensing the same substance and positioned in different planes or surfaces of the device 90. The position of the sensors 200 in different and multiple planes greatly reduces the likelihood of more than one sensor failing, for example by being clogged by debris from the device 90 being dropped. The monitoring device 90 may have more than one sensor 200 for each substance to be detected, i.e., the device 90 may detect more than one substance. The sensors 200 for each substance may be positioned on more than one plane or surface of the device 90. For example, the device 90 may have two sensors 200a and 200b for H2S positioned on different surfaces or planes, e.g., one on the top and one on the side, of the device 90 and two sensors 200c and 200d for oxygen positioned on different surfaces or planes of the device 90, e.g., one on top and one on the side.

Figure 2:
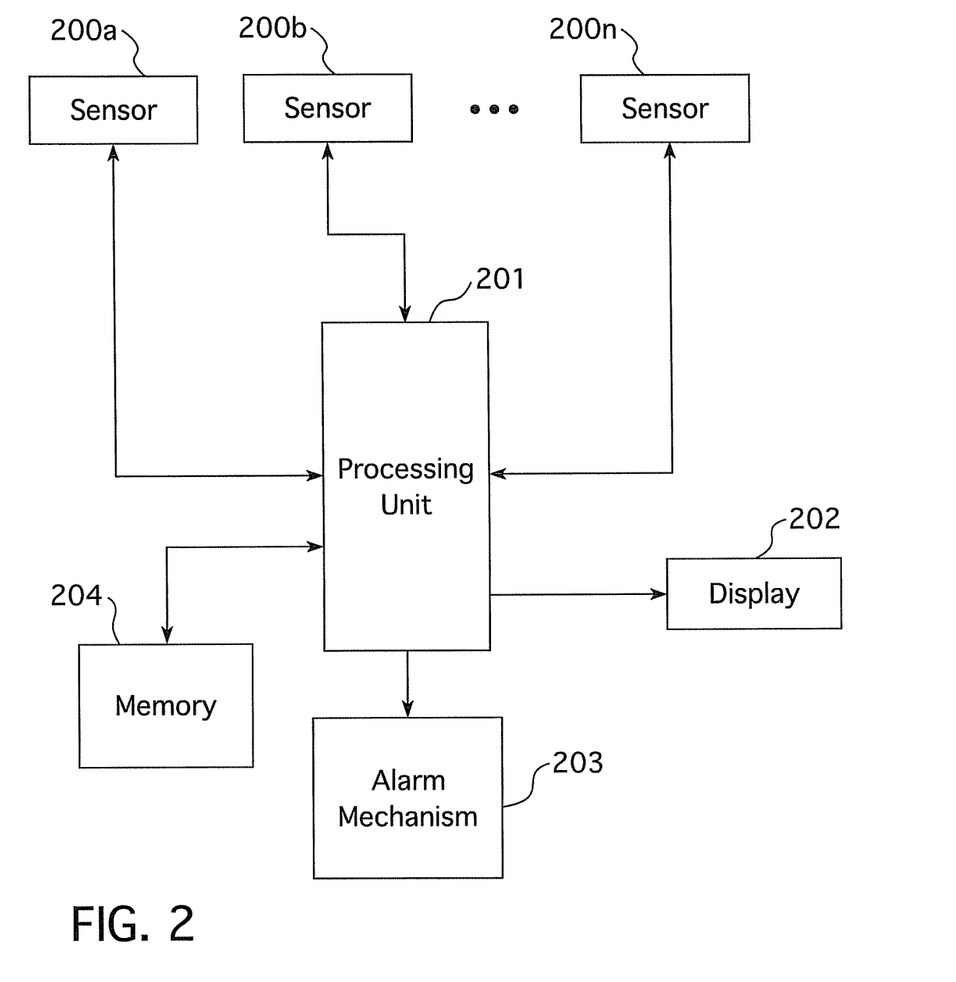
FIG. 2 shows a block diagram illustrating a few of the components of the monitoring device according to various embodiments of the present invention.

In another embodiment the monitoring device 90, as shown in FIG. 2, has a plurality of sensors 200a-n that detect the same substance. One benefit of using more than one sensor 200 for each substance to be detected is reduction in the frequency of bump testing and calibration of the monitoring devices. As an example, in practice monitoring device types typically used for gas detection have been found to fail at a rate of 0.3% a day based on field analysis data and thus daily bump tests have been mandated; however, equivalent safety may be gained with two sensors by bump testing every week, thereby reducing bump testing by seven fold.

In further embodiments, the monitoring device 90, as shown in FIG. 2, has a processing unit 201; a plurality of sensors 200a-n that sense the same substance, such as, for example and without limitation, a gas; a display 202; an alarm 203 that would generate an alarm, for example and without limitation, an audio, visual, and/or vibratory alarm; and a memory 204 to store, for example and without limitation, historic sensor and calibration/bump test data. The processing unit 201 interfaces with the sensors 200a-n and determines the actual reading to be displayed. The actual reading may be, for example and without limitation, the maximum, minimum, arithmetic, mean, median, or mode of the sensor 200a-n readings. The actual reading may be based on artificial intelligence (AI) logic. The AI logic mechanism takes into account, for example and without limitation, the readings from the plurality of sensors 200a-n, historic sensor performance data in the memory 204, span reserve of the sensor 200, gain of the sensor 200, temperature, etc., to determine the actual reading. In another example, as an alternative to the displayed actual reading being the maximum of the aggregate of the n sensors 200a-n, the displayed actual reading may be calculated as follows, where R denotes the displayed reading and $R_i$ denotes the reading sensed by sensor i:

$$R = \sqrt[k]{\frac{\sum_{i=0}^{n} R_i^k}{n}}.$$

Then, the processing unit may display possible actions that need to be taken based on the actual reading derived, for example and without limitation, activate the alarm, request calibration by user, indicate on the display that the sensors are not functioning properly, indicate the current reading of gas or other substance in the environment, auto calibrate sensors that are out of calibration, etc.

One example of the artificial intelligence logic method would be for the greater readings of the two sensors 200a and 200b or the greater readings of a multitude of sensors 200a-n to be compared with a threshold amount, and if the sensor reading crosses the threshold amount, an alarm mechanism would be generated. Another example of AI logic entails biasing the comparison between the sensor readings and the threshold amount by weights that are assigned based on the current reliability of the sensors 200a-n, i.e., a weighted average. These weights can be learned, for example and without limitation, from historic calibration and bump test performance. Standard machine learning, AI, and statistical techniques can be used for the learning purposes. As an example, reliability of the sensor 200 may be gauged from the span reserve or alternatively the gain of the sensor 200. The higher the gain or lower the span reserve, then the sensor 200 may be deemed less reliable. Weights may be assigned appropriately to bias the aggregate substance concentration reading (or displayed reading) towards the more reliable sensors 200a-n. Consider R to denote the displayed reading, $R_i$ to denote the reading sensed by sensor I, and $w_i$ to denote the weight associated by sensor i:

$$R = \frac{\sum_{i=1}^{n} w_i * R_i}{n}$$

where the weight $w_i$ ($0 < w_i \geq 1$) is proportional to span reading of sensor i or inversely proportional to the gain $G_i$. Alternatively, $w_i$ can be derived from historical data analysis of the relationship between the gain $w_i$ and span reserve or gain $G_i$. Historical data of bump tests and calibration tests performed in the field, for example and without limitation, can be used to derive this data.

Figure 3:
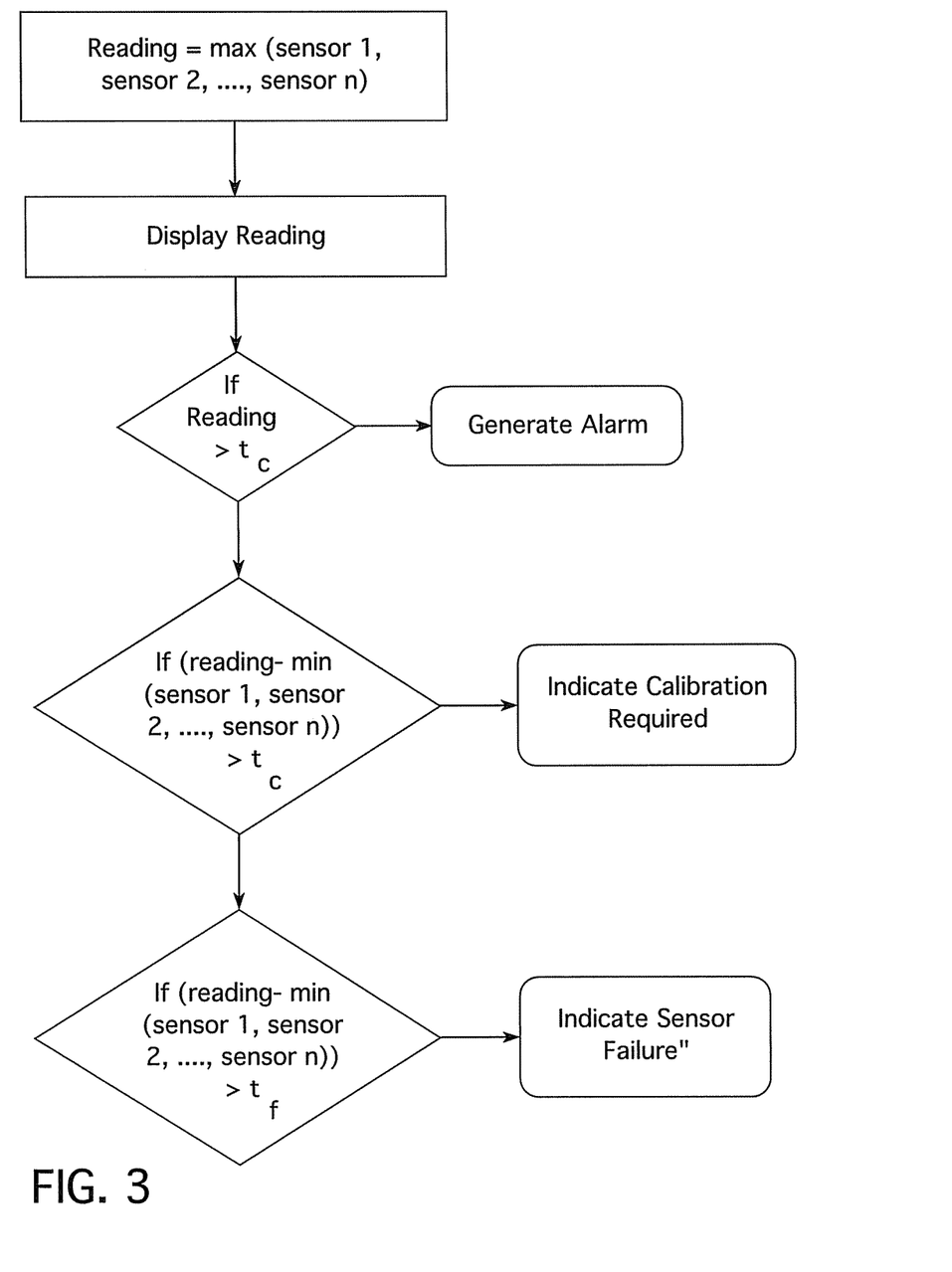
FIG. 3 illustrates a flowchart of an example AI logic according to various embodiments of the present invention.

In addition, as illustrated in FIG. 3, if the difference in readings between any two or more sensors 200 is greater than some threshold value $t_c$, which could be determined in absolute terms or relative percentage terms and may vary by substance, then the monitoring device 90 would generate an alarm or visual indication in the display 202 requesting a calibration by docking on a docking station or manually be performed on the device 90. Further, if the difference in readings is greater than some higher threshold value $t_f$, the monitoring device 190 would generate an alarm and or indicate on the display 202 a message indicating a sensor failure.

In some circumstances, for example and without limitation, in the case of an oxygen sensor, the minimum reading of a multitude of sensors 200$a$-$n$ may be used to trigger an alarm to indicate a deficient environment.

In another embodiment, the monitoring device 90 may have an orientation sensor, such as, for example and without limitation, an accelerometer, that would allow the artificial intelligence logic to factor in relative sensor orientation to account for the fact that heavier than air gases, for example, would affect sensors in a lower position more than on a higher position and lighter than air sensors would. The degree of adjustment to the reading based on orientation can be learned, for example and without limitation, from the calibration data, field testing, distance between sensors, etc. and used to adjust readings from multiple positions on the device 90 to give the most accurate reading at the desired location, such as the breathing area of a user or a specific location in a defined space using the environmental monitoring device 90 as a personnel protection device.

Figure 4A:
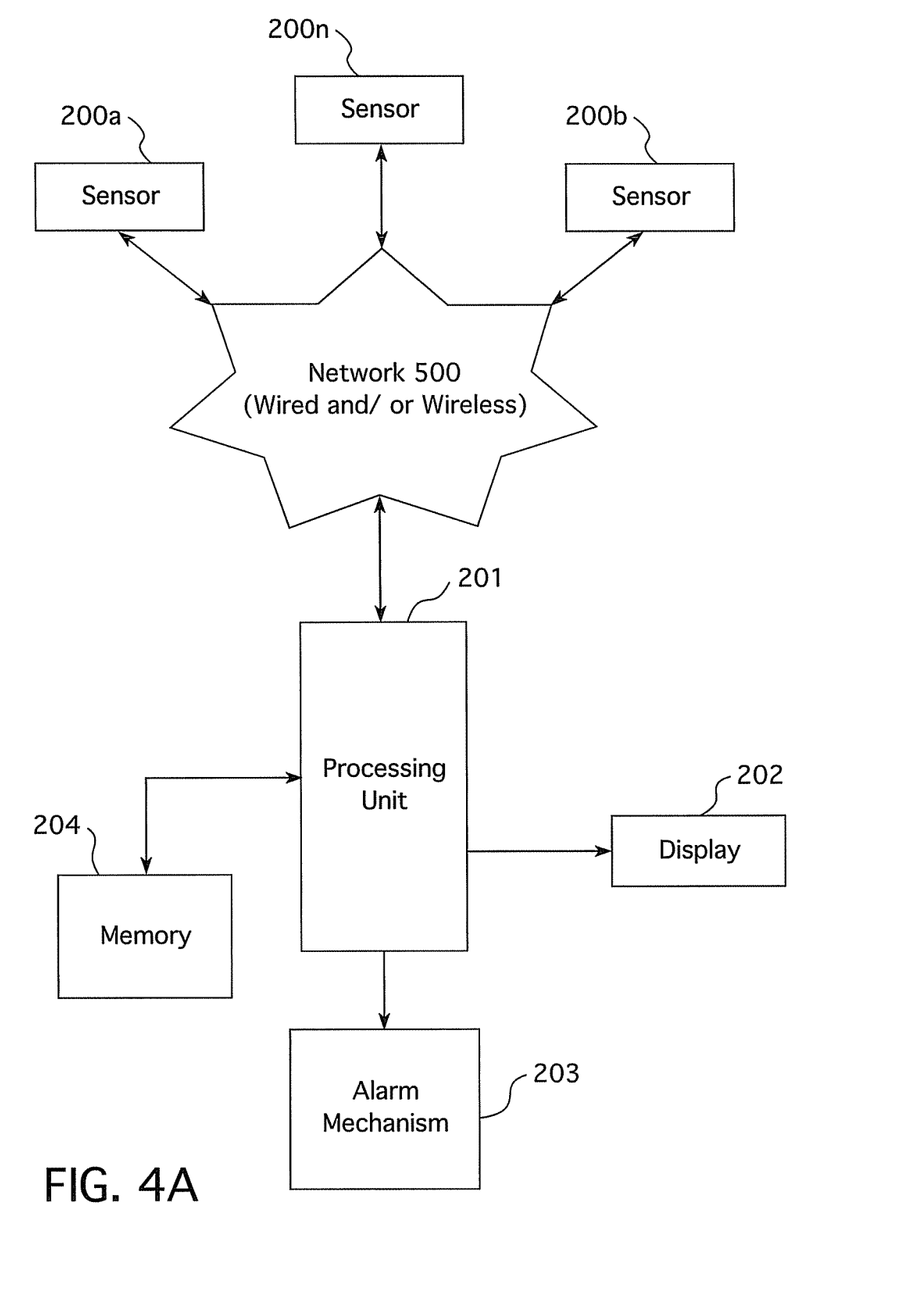
FIG. 4A illustrates a monitoring device with the plurality of sensors housed in multiple housings and connected to a central processing unit and FIG. 4B illustrates a network of monitoring devices according to various embodiments of the present invention.
Figure 4B:
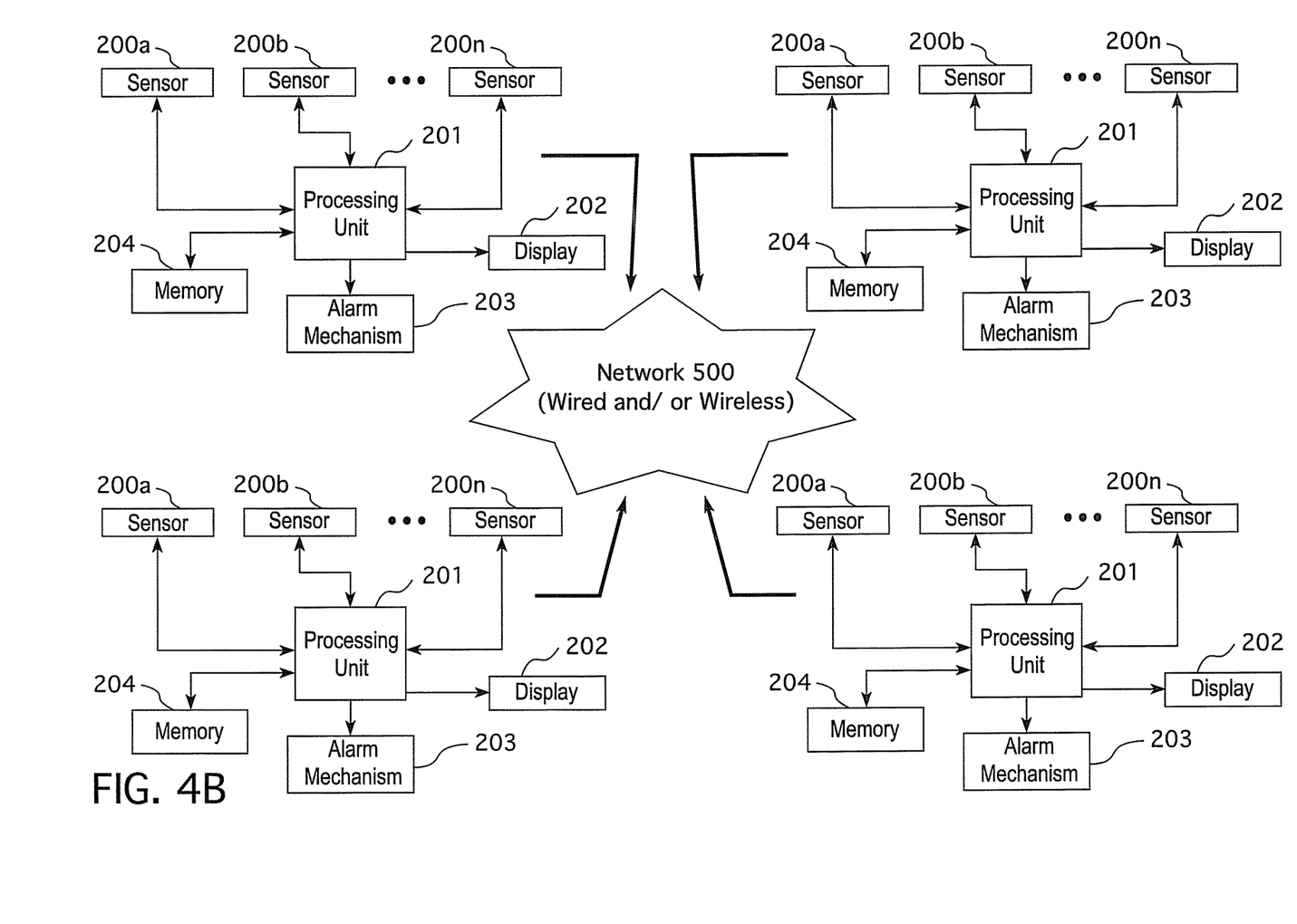

Another embodiment pertains to a network 500 having the plurality of sensors 200$a$-$n$ that detect a single substance housed in separate enclosures, placed in the vicinity of one another, e.g., from inches to feet depending on the area to be monitored, and communicate with one another directly and/or the central processing unit through a wireless or wired connection. See FIGS. 4A and 4B. Each of the housings 104 may have a separate processing unit 201, memory 204, and AI processing logic, as shown in FIG. 4B. Alternatively, or in combination, sensor units would share a central processing unit 201 and memory 204, as shown in FIG. 4A.

Based on the plurality of sensor readings 200$a$-$n$, the processing unit, using standard AI and machine learning techniques, etc., will adjust the gain of the sensors 200$a$-$n$ to match closer to the majority of sensors 200$a$-$n$ for each substance, i.e., minimize variance among the sensors. The variance may be, for example and without limitation, a statistical variance, other variance metrics such as Euclidean distance, or calculated from the average, weighted average, mean, median, etc. readings of the sensors. This would allow auto or self calibration of outlying sensors 200$a$-$n$ without the use of calibration gas using a manual method or a docking station. In an example, if n sensors 200$a$-$n$ sensing a particular gas, such as H2S, are considered and $R_i$ is the reading that represents the concentration of H2S sensed by sensor i and M is the median value of the reading among the n sensors, then the gain, given by $G_i$, of each sensor can be adjusted so that the reading $R_i$ moves towards the median value by a small amount given by weight w(0<w≥1). For each sensor i in (1,n):

$$G_i = G_i * \left(w * \frac{R_i}{M}\right)^{G_i = G_i *\left(w*\frac{R_i}{M}\right)}$$

Performing such gain adjustment whenever the monitoring device 90 is exposed to a substance in the field, for example, as part of day-to-day operation will reduce the frequency of calibrations required, thus saving money both directly from the reduction in calibration consumption, such as gas, and also costs involved in taking time away to perform the calibration. Current monitoring devices that use a single gas sensor for detecting each gas type require a more frequent calibration schedule, thereby incurring significant costs.

While presently preferred embodiments of the invention have been shown and described, it is to be understood that the detailed embodiments and Figures are presented for elucidation and not limitation. The invention may be otherwise varied, modified or changed within the scope of the invention as defined in the appended claims.

EXAMPLE

The following discussion illustrates a non-limiting example of embodiments of the present invention.

A single gas monitor that is used as a small portable device worn on the person and used primarily as personal protection equipment may be used to detect the gases within the breathing zone of the bearer of the device. The gas monitor is designed to monitor one of the following gases:

| Measuring Ranges: | | | |
|---|---|---|---|
| Gas | Symbol | Range | Increments |
| Carbon Monoxide | CO | 0-1,500 | 1 ppm |
| Hydrogen Sulfide | $H_2S$ | 0-500 ppm | 0.1 ppm |
| Oxygen | $O_2$ | 0-30% of volume | 0.1% |
| Nitrogen Dioxide | $NO_2$ | 0-150 ppm | 0.1 ppm |
| Sulfur Dioxide | $SO_2$ | 0-150 ppm | 0.1 ppm |

The sensors are placed on two separate planes of the monitoring device, for example as depicted in FIGS. 1A-C. The gas concentration of the reading is calculated in the following manner:

$$reading = \frac{\sqrt{SensorReading1^5 + SensorReading2^5}}{2}$$

If the reading is higher (or lower in the case of oxygen) than a user defined alarm threshold, then an audio and visual alarm is generated.

Further, if reading>0.5*abs(alarmThreshold−normalReading) and if $$0.3 \leq \frac{abs(sensorReading1 - sensorReading2)}{max(sensorReading1, sensorReading2)} \leq 0.5$$

then an auto calibrate function based on gain as described below is performed. The auto calibration may be done, based on a user defined setting in the monitoring device, without further input from the user of the monitoring device, and/or the user will be informed that the gas monitor has detected an anomaly and requests permission to auto calibrate.

If $$\frac{abs(sensorReading1 - sensorReading2)}{max(sensorReading1, sensorReading2)} > 0.5$$

then a message is displayed to the user to calibrate the gas monitor immediately using a calibration gas.

Gain of each of the sensors is modified as follows in the auto or self calibration process:

$$sensorGain^{new} = sensorGain^{old} + 0.1 * \frac{max(sensorReading1, sensorReading2)}{min(sensorReading1, SensorReading2)}$$

What is claimed is:

1. A system, comprising:
a plurality of monitoring devices, wherein each of the plurality of monitoring devices comprises at least one sensor configured to detect a substance and to generate an output signal indicative of a concentration of the substance in response to a detection of the substance, wherein the at least one sensor in each of the plurality of monitoring devices is configured to detect a same substance, wherein an amount of the substance has not been determined prior to the detection of the substance;
a processing unit, wirelessly coupled to the at least one sensor in each of the plurality of monitoring devices, configured to:
receive each output signal from each of the at least one sensor in each of the plurality of monitoring devices in response to the detection of the sub stance;
generate a detection signal for the substance indicative of the amount of the substance based on the output signals from the at least one sensor in each of the plurality of monitoring devices;
determine a corresponding gain of each of the at least one sensor in each of the plurality of monitoring devices and an overall gain of a majority of the at least one sensor in each of the plurality of monitoring devices based on the determined corresponding gains;
generate a calibration action responsive to any of the output signals deviating by an amount from the detection signal, wherein the calibration action comprises only adjusting a corresponding gain of a corresponding deviating sensor to correspond with the determined overall gain of the majority of the at least one sensor in each of the plurality of monitoring devices;
determine a weight of each of the at least one sensor configured to indicate a reliability of each of the at least one sensor, wherein the weight for each of the at least one sensor is determined based on at least one of a span reserve of the at least one sensor, a historic calibration performance of the at least one sensor, or a historic bump test performance of the at least one sensor; and
determine an aggregate substance concentration reading by aggregating the output signals from each of the at least one sensor biased toward output signals from sensors indicated as being more reliable based on the weight.

2. The system of claim 1, further comprising, an alarm operably coupled to the processing unit, the alarm configured to be activated responsive to the detection signal deviating from a level that corresponds to a predetermined concentration of the substance.

3. The system of claim 1, wherein the plurality of monitoring devices are configured to wirelessly communicate with one another.

4. The system of claim 1, further comprising, a display operably coupled to the processing unit configured to display a reading for the substance in accordance with the output signals.

5. The system of claim 4, wherein the reading is at least one of a maximum, a minimum, a mean, a median, or a mode of the output signals.

6. The system of claim 4, wherein the reading is based on artificial intelligence (AI) logic that takes into account at least one of the output signals from the sensors, a historic sensor performance data, a span reserve of the sensors, a gain of the sensors, or a temperature.

* * * * *

UNITED STATES PATENT AND TRADEMARK OFFICE
CERTIFICATE OF CORRECTION

PATENT NO. : 10,557,839 B2
APPLICATION NO. : 15/376823
DATED : February 11, 2020
INVENTOR(S) : Raghu Arunachalam Page 1 of 1

It is certified that error appears in the above-identified patent and that said Letters Patent is hereby corrected as shown below:

On the Title Page

On the page 3, in Column 1, item (56) under "Other Publications", Line 2, delete "Mul tigas" and insert -- Multigas --, therefor.

On the page 3, in Column 2, item (56) under "Other Publications", Line 15, delete "Pricipal" and insert -- Principal --, therefor.

In the Specification

In Column 5, Line 13, delete "and or" and insert -- and/or --, therefor.

In Column 5, Line 64, delete "$G_{i,}$," and insert -- $G_i$, --, therefor.

In the Claims

In Column 7, Line 35, in Claim 1, delete "sub stance;" and insert -- substance; --, therefor.

Signed and Sealed this
Twenty-eighth Day of April, 2020

Andrei Iancu
*Director of the United States Patent and Trademark Office*